United States Patent
Wu et al.

(10) Patent No.: US 6,254,632 B1
(45) Date of Patent: Jul. 3, 2001

(54) IMPLANTABLE MEDICAL DEVICE HAVING PROTRUDING SURFACE STRUCTURES FOR DRUG DELIVERY AND COVER ATTACHMENT

(75) Inventors: Steven Z. Wu, Santa Clara; Sameer Harish, Fremont; Deborra Sanders-Millare; Judy A. Guruwaiya, both of San Jose, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/675,044

(22) Filed: Sep. 28, 2000

(51) Int. Cl.⁷ ...................................................... A61F 2/06
(52) U.S. Cl. ............................................................ 623/1.15
(58) Field of Search ................................ 623/1.13, 1.15, 623/1.16, 1.44, 1.34, 1.1, 1.42, 1.12, 1.11

(56) References Cited

U.S. PATENT DOCUMENTS

| | | | |
|---|---|---|---|
| 4,368,088 | * 1/1983 | Asakura et al. | 156/143 |
| 4,733,665 | 3/1988 | Palmaz | 128/343 |
| 4,800,882 | 1/1989 | Gianturco | 128/343 |
| 4,886,062 | 12/1989 | Wiktor | 128/343 |
| 5,123,917 | 6/1992 | Lee | 623/1 |
| 5,282,824 | 2/1994 | Gianturco | 606/198 |
| 5,421,995 | 6/1995 | Norcross | 210/86 |
| 5,464,650 | 11/1995 | Berg et al. | 427/2.3 |
| 5,527,337 | 6/1996 | Stack et al. | 606/198 |
| 5,681,345 | * 10/1997 | Euteneuer | 623/1 |
| 5,700,286 | 12/1997 | Tartaglia | 623/1 |
| 5,713,949 | 2/1998 | Jayaraman | 623/1 |
| 5,759,192 | 6/1998 | Saunders | 606/194 |
| 5,766,710 | 6/1998 | Turnlund et al. | 428/36.1 |
| 5,769,883 | * 6/1998 | Buscemi et al. | 623/1 |
| 5,842,164 | 12/1998 | Frantzen et al. | 623/1 |
| 5,843,172 | * 12/1998 | Yan | 623/1 |
| 5,873,904 | * 2/1999 | Ragheb et al. | 623/1 |
| 5,893,867 | * 4/1999 | Bagaoisan et al. | 623/1 |
| 5,948,018 | 9/1999 | Dereume et al. | 623/1 |
| 5,948,191 | 9/1999 | Solovay | 156/86 |
| 6,010,530 | 1/2000 | Goicechea | 623/1 |
| 6,190,404 | * 2/2001 | Palmaz et al. | 623/1 |

FOREIGN PATENT DOCUMENTS

WO 98/23228   6/1998   (WO) ................................. A61F/2/06

* cited by examiner

*Primary Examiner*—Henry J. Recla
*Assistant Examiner*—(Jackie) Tan-Uyen T. Ho
(74) *Attorney, Agent, or Firm*—Skjerven Morrill MacPherson LLP; James E. Parsons; Signe M. Holmbeck

(57) ABSTRACT

A method for forming an implantable medical device, such as a stent, covered stent, or synthetic stent graft, is provided. Protruding structures are formed on a surface of the device. The protruding structures have a central depression region surrounded by a lip. The protruding structures can have a variety of shapes, including circular and ovular shapes, or the protruding structure can form a groove. The protruding structures can be used to engage a cover. Glue can be added to the protruding structures to help secure the cover. The protruding structures can also contain a therapeutic substance or substances for release in situ. The protruding structures can be formed using a laser discharge to create a hole in the stent surface followed by directing a pressurized stream of grit at the surface.

31 Claims, 8 Drawing Sheets

IMPLANTABLE MEDICAL DEVICE HAVING PROTRUDING SURFACE STRUCTURES FOR DRUG DELIVERY AND COVER ATTACHMENT

BACKGROUND OF THE INVENTION

1. Field of the Invention

This invention relates generally to medical devices, such as stents and covered stents. More particularly, the present invention is directed to a structure on the surface of the stent and a method for forming the structure.

2. Description of the Background

Certain implantable medical devices, such as stents and grafts, are implanted within blood vessels and other body passageways to treat disease conditions such as stenoses, occlusions, and aneurysms.

Stents are scaffoldings, usually cylindrical in shape that function to physically support, and, if desired, expand the wall of the passageway. Typically, a stent consists of two or more struts or wire support members connected together into a lattice-like or open weave frame.

Most stents are compressible for insertion through small cavities, and are delivered to the desired implantation site percutaneously via a catheter or similar transluminal device. Once at the treatment site, the compressed stent is expanded to fit within or expand the lumen of the passageway. Stents are typically either self-expanding or are expanded by inflating a balloon that is positioned inside the compressed stent at the end of the catheter. Intravascular stents are often deployed after coronary angioplasty procedures to reduce complications, such as the collapse of arterial lining, associated with the procedure.

In addition to providing physical support to passageways, stents are also used to carry therapeutic substances for local delivery of the substances to the damaged vasculature. For example, anticoagulants, antiplatelets, and cytostatic agents are substances commonly delivered from stents and are used to prevent thrombosis of the coronary lumen, to inhibit development of restenosis, and to reduce post-angioplasty proliferation of the vascular tissue, respectively. The therapeutic substances are typically either impregnated into the stent or carried in a polymer that coats the stent. The therapeutic substances are released from the stent or polymer once it has been implanted in the vessel.

A problem with delivering therapeutic substances from a stent is that, because of the limited size of the stent, the total amount of therapeutic substance that can be carried by the stent is limited. Furthermore, when the stent is implanted into a blood vessel, much of the released therapeutic substance enters the blood stream before it can benefit the damaged tissue. To improve the effectiveness of the therapeutic substances, it is desirable to maximize the amount of therapeutic substance that enters the local vascular tissue and minimize the amount that is swept away in the bloodstream.

The lattice-like structure of the stent leaves spaces defined by the struts that form the stent. These spaces can allow plaque from the lesion to fall through the stent and enter the blood stream during stent deployment. The spaces can also permit malignant tissue growth through the stent openings into the body passageway and can allow undesired contact between blood flowing through the blood vessel and damaged portions of the vessel intima. Covered stents, in which a polymeric material surrounds and is attached to the stent, have been proposed to alleviate the problems associated with stent openings.

Diseased vessels are also treated with grafts. Grafts are generally tubular in shape and are used to replace or create an anatomical passageway to provide a new conduit for fluid, e.g. blood. Grafts are often made from a portion of a vein, but can also be constructed from a synthetic material to form a synthetic graft. Like stents, synthetic grafts can be positioned percutaneously via a catheter, for instance, to be placed at the site of an aneurysm to prevent further dilation and possible rupture of the diseased vessel.

In certain instances, the graft material alone does not provide enough structural support for the graft, causing the graft to collapse and occlude or impede the flow of blood through the vessel. To counter this problem, a similar, even identical, structure to the covered stent, in which a stent is placed within the synthetic graft material, has been proposed to improve the structural strength of grafts. This structure is sometimes referred to as a synthetic stent graft. Stents are also placed at the ends of synthetic grafts to help secure the ends of the synthetic graft to vessel walls.

Examples in the patent literature of covered stents include U.S. Pat. No. 5,948,191 titled "Low profile, thermally set wrapped cover for a percutaneously deployed stent" issued to Solovay; U.S. Pat. No. 5,123,917 titled "Expandable intraluminal vascular graft" issued to Lee; U.S. Pat. No. 5,948,018 titled "Expandable supportive endoluminal grafts" issued to Dereume et al.; U.S. Pat. No. 5,282,824 titled "Percutaneous stent assembly" issued to Gianturco; U.S. Pat. No. 5,843,164 titled "Intraluminal stent for attaching a graft" issued to Franzen; and U.S. Pat. No. 6,010,530 titled "Self-expanding endoluminal prosthesis" issued to Goicoechea.

A problem with covered stents and synthetic stent grafts is keeping the stent covering attached to the stent. During expansion of the prosthesis, the covering pulls isometrically, causing the cover to shorten and possibly detach from the stent.

Currently, covers are attached to stents by stitching or gluing, or by wholly embedding the stent into the polymeric cover material. When stitches are used, the cover is typically punctured at the stitch site, leaving an opening and a weak place in the cover that may tear or rip when the covered stent is expanded. Using glue instead of stitches eliminates these problems, however, glue can be difficult to keep in place on the stent when attaching the cover material. Furthermore, in some cases, the glue itself does not provide a strong enough hold to keep the cover attached. When the stent is wholly embedded into the cover material, the covering is on both the inside and outside of the stent and may cause the profile of the covered stent to be larger than desired.

SUMMARY

In the embodiments of the present invention, protruding structures are provided for the surface of a stent or other implantable medical device. The protruding structures can be used with covered stents and synthetic stent grafts to engage and secure the cover, advantageously improving retention of the covering. The protruding structures can also be used to keep glue in place on the stent when attaching the covering. The protruding structures can also be used to deliver therapeutic substances from the stent directly to the lumen wall and advantageously minimize the amount of therapeutic substance swept away in the blood stream.

An exemplary protruding structure includes a depression region having a bottom surface that is fully or partially surrounded by a protruding lip. The depression region is approximately centrally located in the protruding structure and the lip is higher than the bottom surface relative to the surface of the stent.

The protruding structure can have a variety of shapes, including a generally circular shape so that the protruding structure forms a crater, and an elongated shape so that the protruding structure forms a groove.

The bottom surface of the protruding structure can be above the surface of the stent or can be beneath the surface of the stent. In general, the distance between the bottom surface of the protruding structure and the stent surface is less than 80% of the distance between the inner and outer surfaces of the stent.

The protruding structures on the stent can contain one or more therapeutic substances. The therapeutic substances can be covered by a polymeric layer, which can reduce the release rate of the therapeutic substances from the stent for a delayed or sustained delivery.

A polymeric cover can be attached to a portion of the stent using the protruding structures, forming a covered stent. The protruding structures engage the cover. A glue can be added to the protruding structures to help secure the cover onto the stent. The cover can contain a therapeutic substance.

The cover can be shaped as a tube, having a first end and an opposing second end and a hollow bore extending longitudinally through the cover from the first to second end. The cover can concentrically enclose the outer surface of the stent. The cover can also be attached to two portions of the stent, one at each end of the cover, that include the protruding structures on their respective surfaces.

In one embodiment of the method within the present invention, the protruding structures can be made by directing a laser discharge at the surface of a stent to form a hole in the stent, and projecting a stream of pressurized grit onto the surface at and around the hole. The pressurized grit can be beads or sand, among other possibilities.

These and other embodiments and aspects of the present invention will be better understood in view of the drawings and the following detailed description.

DETAILED DESCRIPTION

In the discussion below, examples of the present invention are provided in the context of stents and grafts. Artisans will appreciate, however, that the present invention also may be used in association with other types of implantable medical devices, such as an implantable disk, joint, or pacemaker, among other possibilities.

Figure 1:
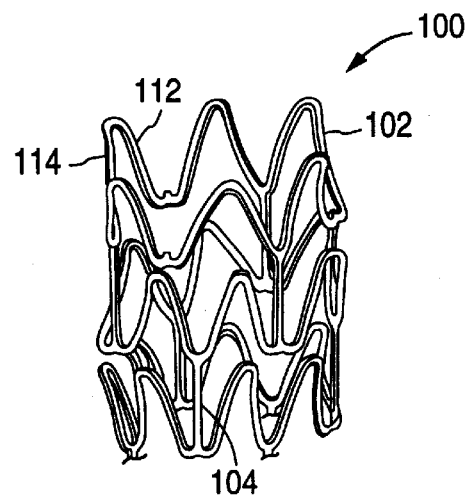
FIG. 1 is a perspective view of an example of a stent in an expanded state.

FIG. 1 illustrates an exemplary stent 100. Stent 100 is a patterned cylindrical device that includes a plurality of radially expanding cylindrical struts 102 disposed generally coaxially and interconnected by connecting struts 104 that are disposed between and connect adjacent cylindrical struts 102. Struts 102 and 104 can be any suitable thickness between the stent outer surface 114 and inner surface 112. Typically thickness (T, illustrated in FIG. 2A) is in the range of approximately 20 μm (0.001 inches) to 200 μm (0.008 inches). Struts 102 and 104 can also have any suitable width (W, illustrated in FIG. 2A), typically in the range 100 μm (0.004 inches) to 1000 μm (0.04 inches). A specific choice of thickness and width depends on the application of the stent. These parameters will vary depending on, for example, the anatomy and size of the target lumen.

The stent may be made of any suitable biocompatible material such as a metallic material or an alloy, examples of which include, but are not limited to, stainless steel, "MP35N," "MP20N," elastinite (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The stent also may be made from bioabsorbable or biostable polymers.

Although stent 100 is illustratively shown in the configuration 100 of FIG. 1, the stent 100 may be of virtually any configuration so long as stent 100 meets the needs of the treatment procedure and, if used as a covered stent, is capable of securely receiving a cover. Other configurations, such as helices, coils, braids, or the like may be utilized depending on the application for the prosthesis. For example, if the prosthesis is to be inserted percutaneously by use of a catheter, the stent will need to be capable of radially compressing and expanding, as discussed above.

In accordance with the various embodiments of the present invention, at least a portion of the outer surface 114 of stent 100 contains protruding structures that have a depression region substantially surrounded by a lip. The lip extends above the plane of the stent surface 114 and above the depression region.

In one embodiment, the protruding structures have approximately circular shapes and are referred to herein as "craters". As illustrated by the exemplary crater 200 in FIG. 2A, an approximately circular depression region 202, located approximately in the center of crater 200, is surrounded by a wall-like lip 204 that extends above the plane of the stent surface 114. The lip 204 has an outer surface 206, and an inner surface 208 that is within depression region 202. The central depression region has a bottom surface 210.

Figure 2A:
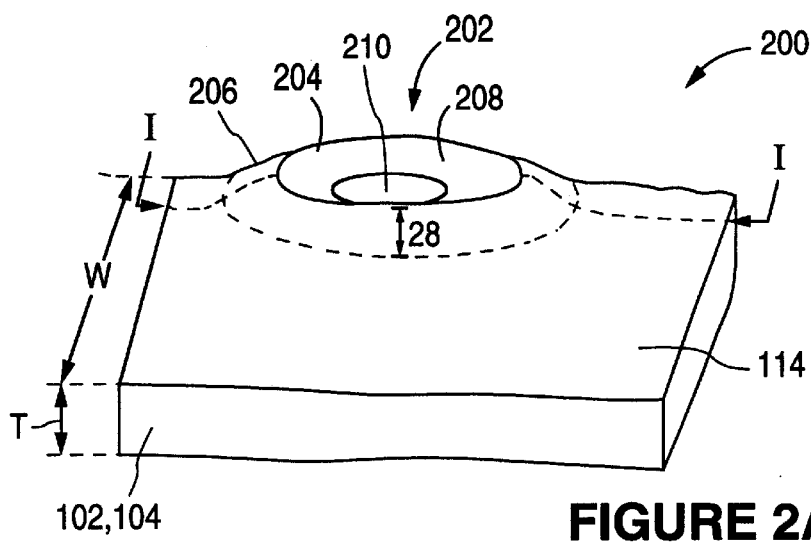
FIG. 2A is a perspective view of a portion of a stent strut with a crater on one of its surfaces.
Figure 2B:
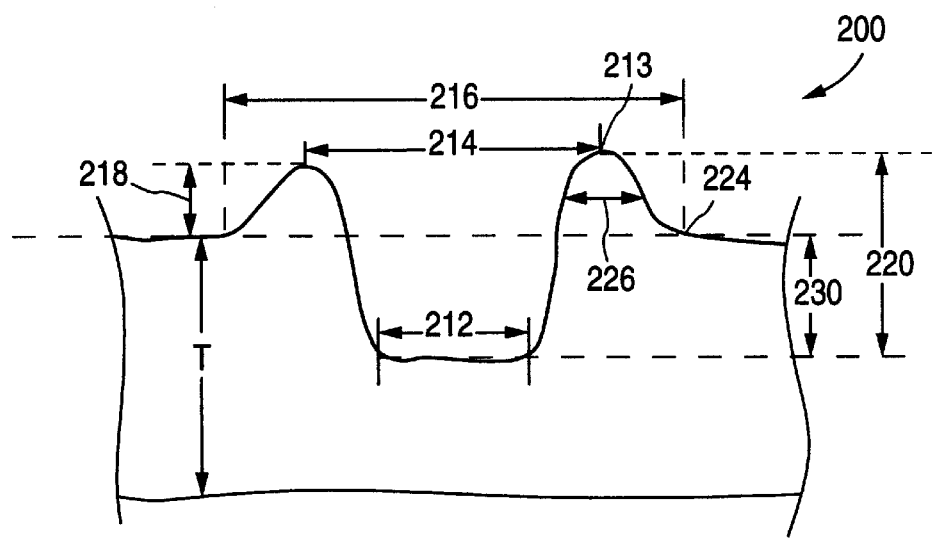
FIG. 2B is a cross-sectional side view of a portion of a stent strut with a crater that has a bottom surface recessed beneath the stent surface.
Figure 2C:
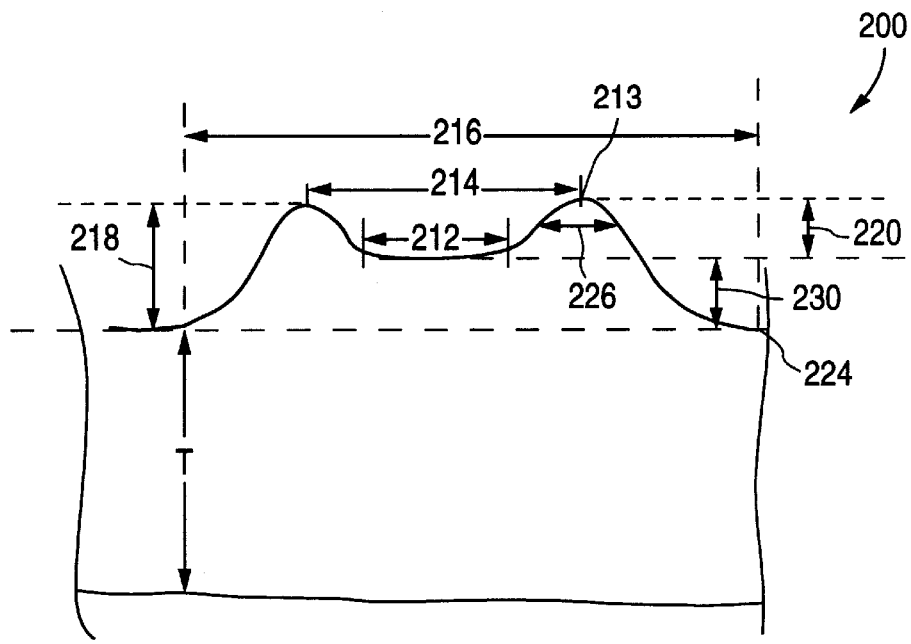
FIG. 2C is a cross-sectional side view of a portion of a stent strut with a crater that has a bottom surface elevated above the stent surface.

Dimensions that define the exemplary crater 200 are illustrated in FIGS. 2B and 2C, which are cross-sectional side views of craters taken along a line II illustrated in FIG. 2A. Dimensions include the diameter 212 of the bottom surface 210; the diameter 214 of the rim 213 of the lip 204; and the diameter 216 of the total crater 200. The height 218 of lip 204 is the distance above the stent surface plane 114 to the top of lip 204. The depth 220 of the depression region 202 is the distance from top of the lip 204 to the bottom surface 210. The depression area has a volume, defined by the volume encompassed by the bottom surface 210, the inner surface 208 of lip 204, and an imaginary top on the crater that is even with the top of the lip 204.

The size of the crater is also defined by the circumference of the rim 213 of the lip 204, the circumference of the bottom surface 210, and the total circumference of the crater 200, which is the circumference around the base 224 of the lip on the stent surface 112, 114. Note that the circumference of the bottom surface 210 may be different, typically smaller, than the circumference of the rim 213 of the lip 204. The total circumference of the crater 200 is typically larger than both the circumference of the bottom surface 210 and the circumference of the rim 213. The lip 204 also has a width 226. Lip width 226 is typically larger at the base 224 of the lip 204 than at the rim 213, although, in some embodiments, it may be constant over the entire lip 204.

Bottom surface 210 of the depression region can be beneath the stent surface plane 114, as illustrated in FIG. 2B, above the stent surface plane, as illustrated in FIG. 2C, or approximately even with the stent surface plane. If the bottom surface 210 of the depression region is beneath the stent surface plane, the recession depth 230 is typically less than 80% of the strut thickness so that the structural integrity of the strut is not compromised.

Figure 3A:
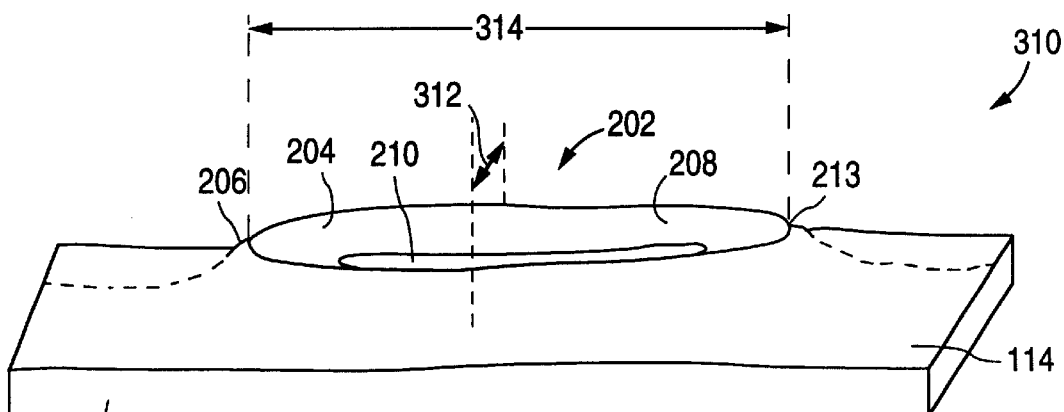
FIG. 3A is a perspective view of a portion of a stent strut with a protruding structure having an ovular shape.
Figure 3B:
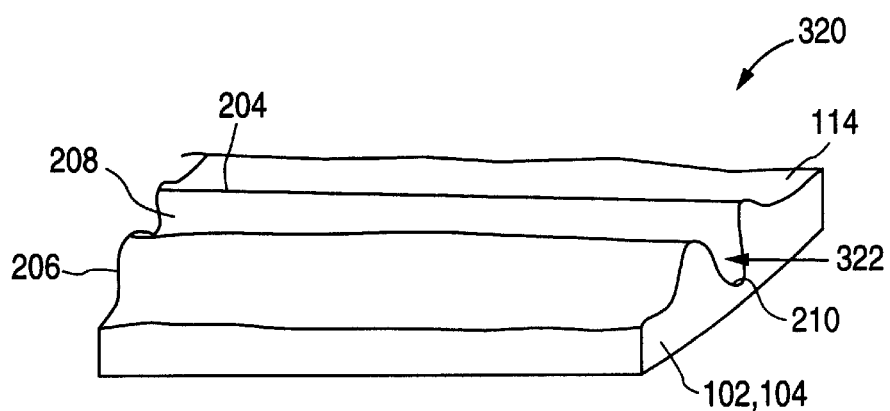
FIG. 3B is a perspective view of a portion of a stent strut with a protruding structure shaped as a groove.
Figure 3C:
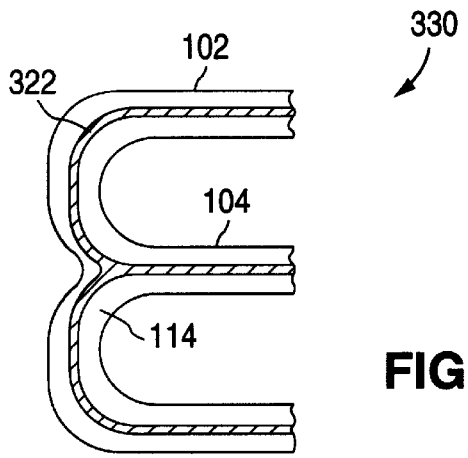
FIG. 3C is a side view of a portion of a stent strut with a groove such as that illustrated in FIG. 3B in the center of the strut and running throughout the strut.
Figure 3D:
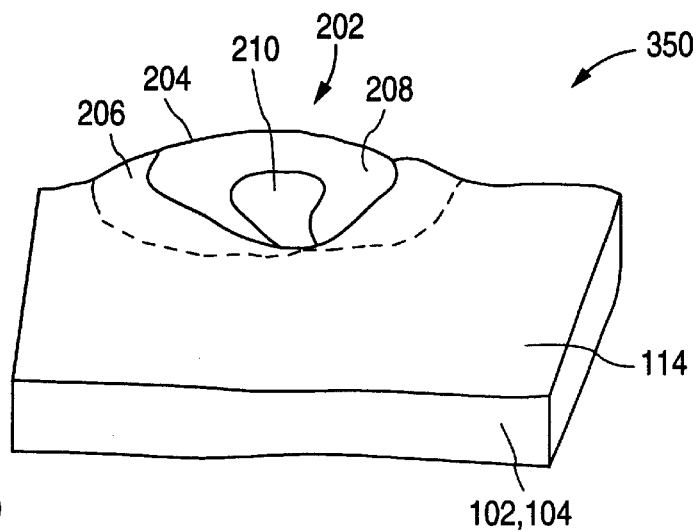
FIG. 3D is a perspective view of a protruding structure having a lip that only partially surrounds the depression region.

In other embodiments, the protruding structure can have a variety of shapes besides the generally circular shape illustrated for crater 200 in FIG. 2A. For example, the protruding structure can be ovular, as illustrated by exemplary protruding structure 310 in FIG. 3A. For such an ovular protruding structure, the size is defined by the length 314 and width 312 of the depression region, and the perimeters of the rim 213, the bottom surface 210, and the total protruding structure 310. In one embodiment, the length 314 of protruding structure 310 is extended, and the protruding structure forms a groove, as illustrated by exemplary groove 320 in FIG. 3B. In one embodiment, the groove 322 is in approximately the center of the stent strut 102, 104. The groove 322 can run along the length of the stent struts 102 and 104, as illustrated in FIG. 3C for a portion of a stent 330. Additional variations of the protruding structures can be formed, for example, the lip may only partially surround the depression region, as illustrated by exemplary protruding structure 350 in FIG. 3D.

The dimensions of the protruding structure depend on the intended application, and hence, dimension and design, of the stent. The largest diameter 216 (or width 312 if the protruding structure is non-circular) is limited by the width W of the stent strut into which the protruding structure is to be formed. Generally, the diameter 216 (or width 312) is between 10% and 80% of the strut width W. The height of the protruding structure, for instance the lip height 218, which is typically less than the strut thickness, will also depend on the design of the stent. For instance, if the stent is to be covered, the cover thickness will be a factor in determining desired lip height, as described below.

In one embodiment, the protruding structures, such as craters 200, are located on the outer surface 114 of the stent and engage the lumen of the passageway when the stent is deployed, to help prevent the stent from slipping out of the treatment site.

A therapeutic substance or substances can be added to all or some of the protruding structures so that the therapeutic substance or substances are released from the stent when implanted in a vessel. The protruding lip will push into the lumen wall and will help to contain the therapeutic substance or substances to prevent loss of therapeutic substance to blood flowing through the vessel. This can advantageously increase the amount of therapeutic substance that is delivered directly to the tissue of the lumen wall.

Figure 4A:
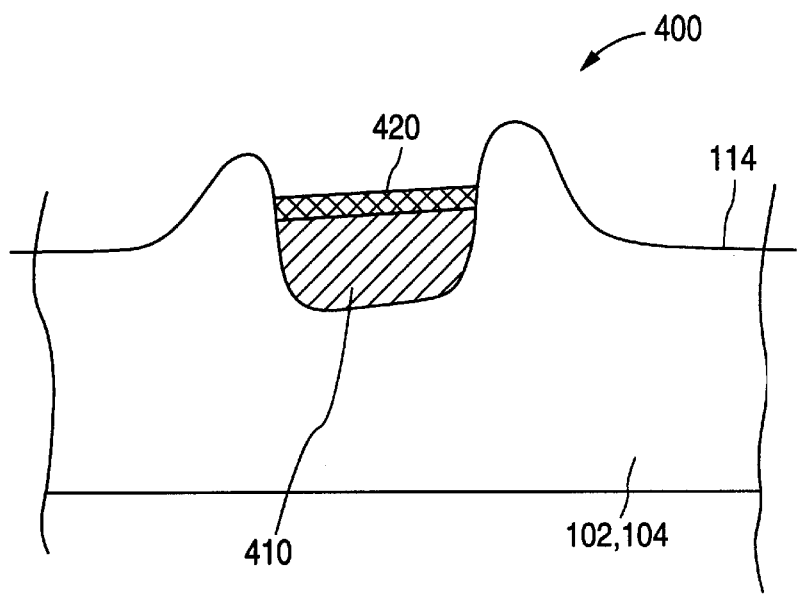
FIGS. 4A and 4B are cross-sectional side views of protruding structures that contain a therapeutic substance or substances that are covered by a polymeric layer.
Figure 4B:
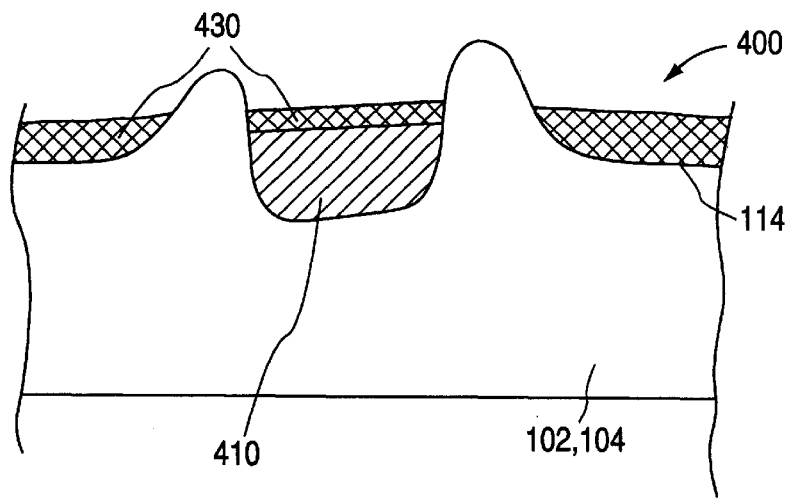

FIGS. 4A and 4B illustrate a cross-sectional side views of a protruding structure 400 that contains the therapeutic substance or substances 410. In one embodiment a top layer of a polymeric material is applied on top of the therapeutic substance or substances to control the release of the substance 410. As illustrated in FIG. 4A, the polymeric layer 420 may be only within protruding structure, or, as illustrated in FIG. 4B, the polymeric layer 430 may cover the stent surface as well.

Polymeric materials that can be used for layer 420, 430 are typically either bioabsorbable or biostable. A bioabsorbable polymer bio-degrades or breaks down in the body and is not present sufficiently long after implantation to cause an adverse local response. Bioabsorbable polymers are gradually absorbed or eliminated by the body by hydrolysis, metabolic process, bulk, or surface erosion. Examples of bioabsorbable, biodegradable materials include but are not limited to polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, and aliphatic polycarbonates. Biomolecules such as heparin, fibrin, fibrinogen, cellulose, starch, and collagen are typically also suitable. Examples of biostable polymers include Parylene®, Parylast®, polyurethane (for example, segmented polyurethanes such as Biospan®), polyethylene, polyethylene teraphthalate, ethylene vinyl acetate, silicone and polyethylene oxide.

In generally, the greater the total volume of depression region 202 on the stent, the greater the amount of therapeutic substance that can be carried by the stent. Therefore, a larger number of protruding structures having a greater depth 220 and greater bottom surface 210 area allows for more therapeutic substance to be carried by the stent. However, the structural integrity of the stent should not be compromised by the protruding structures, and therefore limits the total volume of depression region 202 of the stent.

Therapeutic substances contained in the protruding structures can include, but are not limited to, antineoplastic, antimitotic, anti-inflammatory, antiplatelet, anticoagulant, antifibrin, antithrombin, antiproliferative, antibiotic, antioxidant, and antiallergenic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S.A., Frankfurt, Germany) methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, seratonin blockers, steroids, thioprotease inhibitors, triazolopyrimidine (a PDGF antagonist), and nitric oxide. An example of an antiallergenic agent is permirolast potassium. Other therapeutic substances or agents that may be used include alpha-interferon, genetically engineered epithelial cells, and dexamethasone. In other examples, the therapeutic substance is a radioactive isotope for prosthesis usage in radiotherapeutic procedures. Examples of radioactive isotopes include, but are not limited to, phosphoric acid ($H_3P^{32}O_4$), palladium ($Pd^{103}$), cesium ($Cs^{131}$), and iodine ($I^{125}$). While the preventative and treatment properties of the foregoing therapeutic substances or agents are well-known to those of ordinary skill in the art, the substances or agents are provided by way of example and are not meant to be limiting. Other therapeutic substances are equally applicable for use with the protruding structures.

In one embodiment, the protruding structures (with or without a therapeutic substance therein) are used on a stent that is covered. The protruding structures engage and secure the cover by providing a mechanical hold for the cover, which prevents the cover from slipping or peeling off of the stent.

Figure 5A:
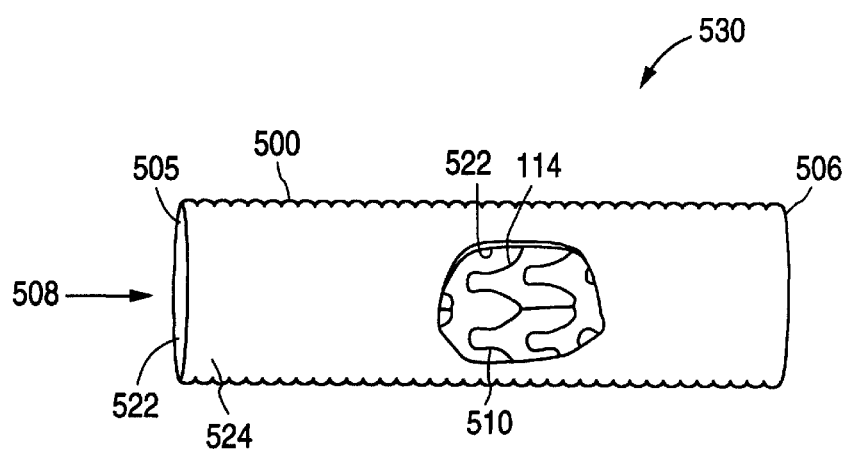
FIG. 5A is a side view of a covered stent illustrating a stent inside of a cover.
Figure 5B:
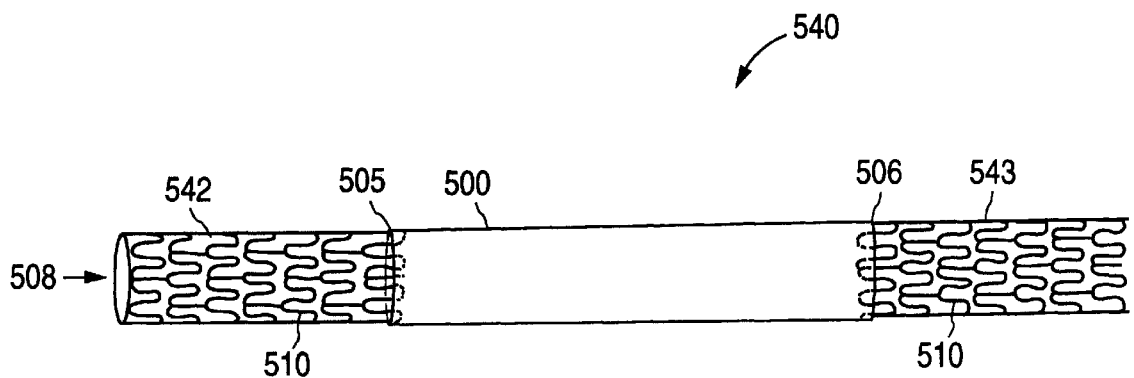
FIG. 5B is a side view of covered stent with the stent in two sections and attached to each end of a cover.
Figure 5C:
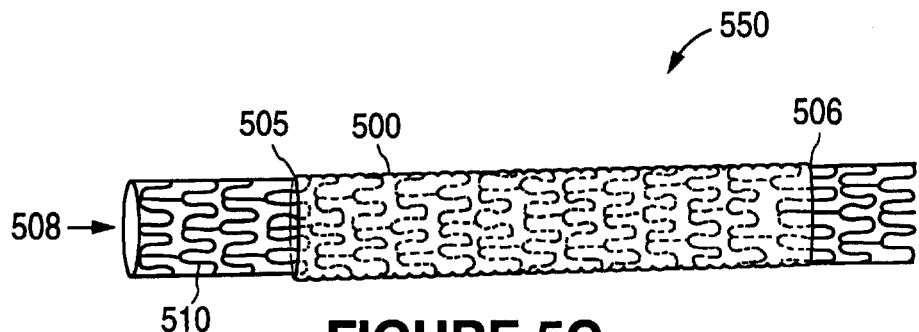
FIG. 5C is a side view of a covered stent in which the stent extends beyond the ends of a cover.

FIGS. 5A–5C illustrate exemplary covered stents, also referred to as synthetic stent grafts. Cover 500 is attached to stent 510 and is typically shaped as a tubular sleeve having an open first end 505 and an open second end 506. A central hollow bore 508 extends longitudinally through the cover 500. Cover 500 has an inner surface 522 and an outer surface 524.

Cover 500 is typically located on the outside of the stent 510, as illustrated by exemplary covered stent 530 in FIG. 5A, such that inner surface 522 of cover 500 is attached to the outer surface 114 of the stent 510. In another embodiment, cover 500 may be on both sides of the stent 510, for instance, the stent struts may be embedded into a polymeric material that forms the cover.

Cover 500 may encompass all or a portion of the stent 510. In one embodiment, illustrated by exemplary covered stent 540 in FIG. 5B, the cover 500 is attached at ends 505, 506 to two stent sections 542, 543, one at each of the cover ends 505 and 506, respectively. In this embodiment, the stent sections at each end of cover 500 can be used to secure the covered stent to the inside of a vessel wall, for instance when treating an aneurysm, such as an abdominal aortic aneurysm.

In another embodiment, illustrated by exemplary covered stent 550 in FIG. 5C, the stent extends all the way through and beyond the ends of the cover, so that portions of the stent are exposed on each end of the cover. Various other combinations of cover (or covers) and stent sections can be used.

Stent 550 may be a single unit, as illustrated in FIGS. 5A and 5C, or may consist of independent sections, as illustrated in FIG. 5B.

Figure 6A:
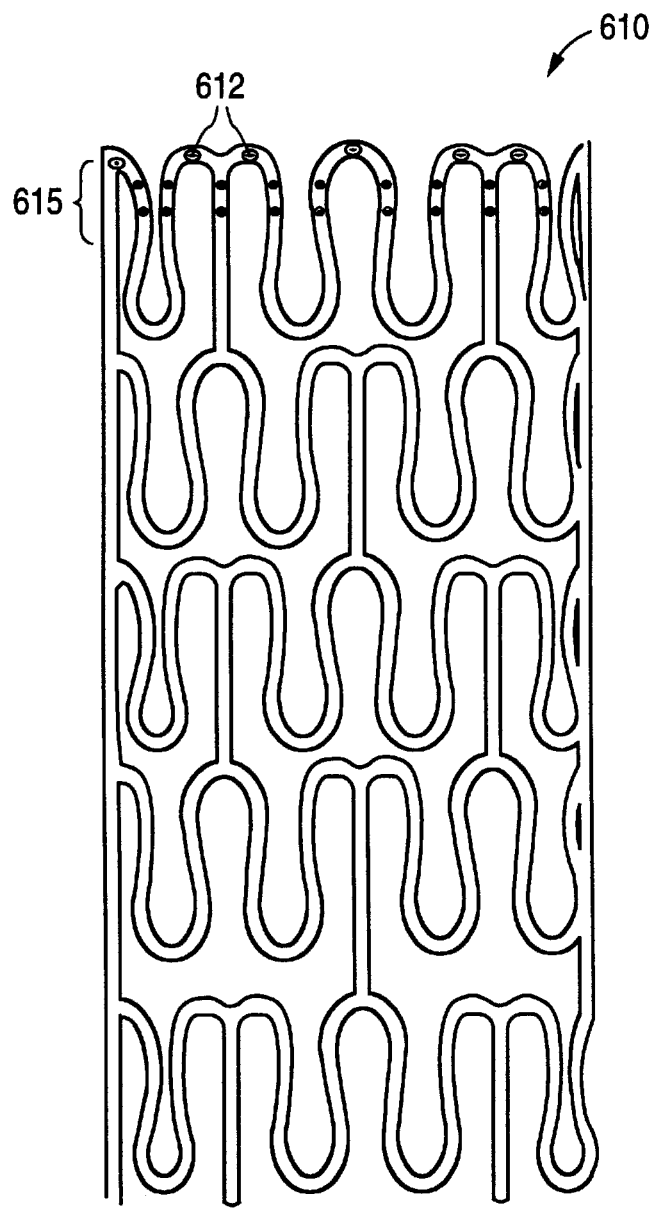
FIG. 6A is a side view of a stent that has protruding structures on only one end of the stent.

The protruding structures can be put onto the stent in varying locations depending on the design of the covered stent. For example, for the covered stent 540 illustrated in FIG. 5B, the cover 500 is attached to only a portion, such as one of the ends of the stent sections 542, 543. In this instance the protruding structures are formed only on those places that will contact and secure the cover 500, such as protruding structures 612 along end 615 of the stent 610 illustrated in FIG. 6A.

Figure 6B:
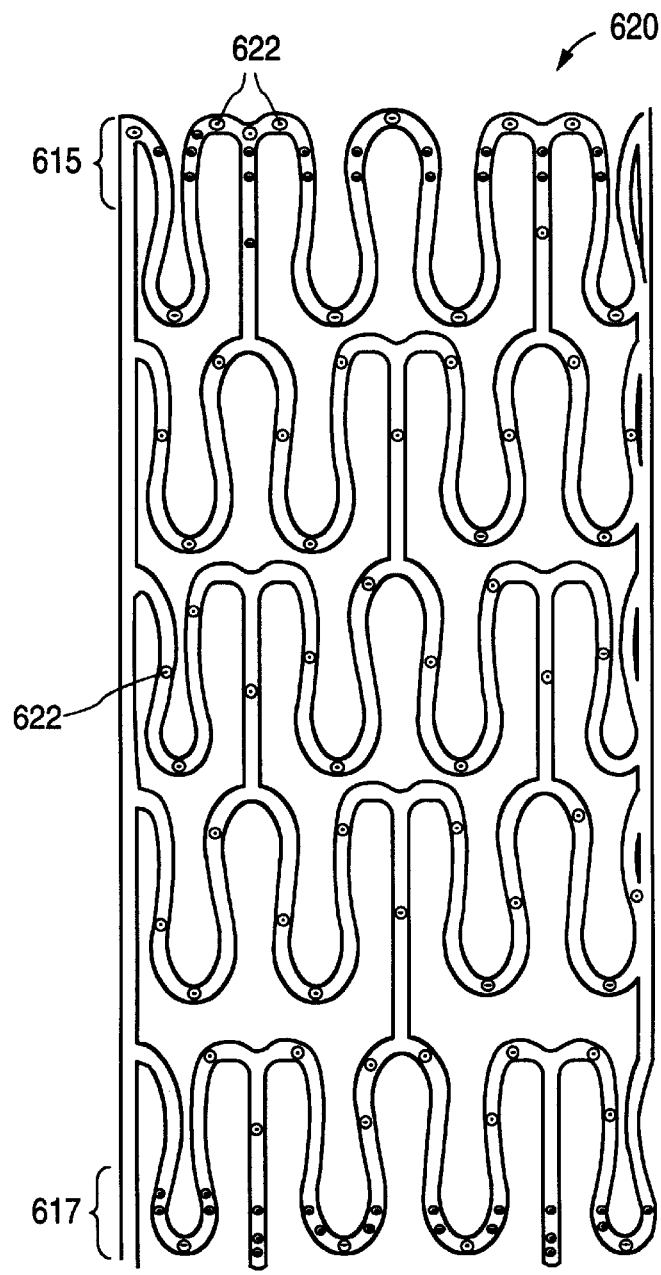
FIG. 6B is a side view of a stent that has a higher density of protruding structures on both of the ends of the stent than in the central portion of the stent.

The protruding structures can be formed on the stent surface in varying densities. Typically, the higher the number of protruding structures, the better the retention of the cover. However, too high a density of the protruding structures may compromise the structural integrity of the stent. The density of structures can also vary depending on the location of the structures on the strut. For example, the stent 620 illustrated in FIG. 6B is for use with a covered stent, such as those illustrated in FIGS. 5A and 5C, in which the entire cover is attached to the stent. The protruding structures 622 can have a higher density at the ends 615 and 617 of the stent 620, where a cover that surrounds the stent will be pulled and shortened the most as the stent expands. Protruding structures 622 on other portions of the stent may reduce the stress on the cover as it is pulled.

In one embodiment, a glue or adhesive is used in addition to the protruding structures to enhance the retention of the cover. The glue can be put into the depression region (202 of FIG. 2A), for instance, by using a syringe, before the cover 500 is put onto the stent 510. The lip 204 will surround and contain the glue, making it less likely that the glue or adhesive will slip off of the stent when the cover is affixed, and protecting the glue from possible chemical and/or mechanical degradation due to blood once the covered stent is implanted. Glues that can be used should be biocompatible and include, but are not limited to, tetrafluoroethyleneperfluoropropylene copolymer (FEP), silicone, and polyurethanes.

The height of the protruding structures and the thickness of the cover depend on the design and application of the covered stent. Covers typically have a thickness in the range of 25 $\mu$m to 500 $\mu$m. In some applications, the height of the protruding structure is less than the cover thickness, so that the structures do not protrude above the cover. In other embodiments, the height is greater than the cover thickness, which may advantageously also allow the protruding structures to anchor the covered stent to the lumen wall. Typically, the protruding structures will indent and deform, but generally not puncture, the cover.

The cover can be preformed before being attached to the stent by methods such as molding, solvent casting, or weaving. The preformed cover can then be attached to the stent by mechanically pressing or crimping the cover onto the stent surface, which may also contain glue, as described above. The preformed cover can also be heat shrunk onto the stent for attachment.

In one embodiment, instead of attaching a preformed cover, the cover is formed directly on the stent. In one method the cover material is dissolved in a solvent or is in a malleable phase and is molded onto or around the stent and allowed to dry or harden to form the covered stent. Alternatively, cover material precursors are dissolved in solution and the solution molded onto the stent and then cross-reacted to form the cover.

The cover 500 can be made from any suitable, biocompatible material, including, but not limited to highly porous materials such as polymers of expanded polytetrafluoroethylene (ePTFE) and polyethylene terephthalate (PET). In an alternate embodiment, cover 500 is made from a less porous material, such as, but not limited to, polyurethanes, absorbable polymers, and combinations or variations thereof. Polyurethanes from which cover 500 may be made include, but are not limited to, Biomer, Biospan, and Elastion. Absorbable polymers from which cover 100 may be made include, but are not limited to, polycaprolactone (PCL), poly(lactic acid) (PLA), poly(glycolic acid) (PGA), polyanhydrides, polyorthoesters, polyphosphazenes, and components of extracellular matrix (ECM). Cover 500 can also be made from autologous fibrin. Teflon and Dacron, materials commonly used to make synthetic vascular grafts, can also be used to form cover 500. Cover 500 may be made of one or more layers of one or more materials.

Cover 500 can also contain a therapeutic substance or substances that may be released from the cover after the covered stent has been implanted. Methods of impregnating a cover with therapeutic substances are well known. Therapeutic substances that can be impregnated in the cover include, but are not limited to, those listed above.

METHOD OF MAKING THE PROTRUDING STRUCTURES ON THE STENT

The lattice pattern of stent 100 can be cut from either a cylindrical tube of the stent material or from a flat piece of the stent material, which is then rolled and joined to form the stent. Methods of cutting the lattice pattern into the stent material include laser cutting and chemical etching, as described in U.S. Pat. No. 5,759,192 issued to Saunders and U.S. Pat. No. 5,421,955 issued to Lau, both patents incorporated herein by reference in their entirety.

The protruding structures can be formed before or after the stent lattice pattern is cut into the stent material. In one embodiment, protruding structures are formed on the stent by using a laser discharge to form holes into the stent in places where it is desired to have a protruding structure, and then directing a stream of pressurized grit at the stent in the area or areas where holes have been drilled.

It is believed that forming the hole with the laser leaves slag material around the outside edges of the drilled hole, which the pressurized grit then forms into the protruding structure shape. As the grit is directed at the stent surface, some of the stent material may be removed. However, some of the grit may be deposited in the central depression region of the hole, protecting that region from the pressurized grit and hence from removal of the stent material.

As an example, a pulsed ND:YAG (neodymium yttrium aluminum garnet) laser system (for example, model KLS 246 supplied by LASAG Industrial Lasers, Arlington, Ill.) that operates at 1064 nm, near infra-red spectrum, may be used to form holes in 316L stainless steel tubing that has a 1.78 mm (0.070 inch) outer diameter and a 152 $\mu$m (0.006 inch) thickness. The laser is pulsed at 1 Hz with a power level of 3.9 watts, which occurs at a voltage setting of 300 Volts. To determine the voltage setting necessary to achieve a given power level (3.9 W in this case), the pulse frequency is set at, for example, 1000 Hz and the voltage setting is adjusted while the power level is measured. Note that the power output for a given voltage setting varies with age of laser and other settings, such as aperture and frequency. The pulse length is 0.05 milliseconds. The feed rate, which is the rate the tubing moves across the laser beam, depends on the stent pattern, but can be nominally 12 inches per minute. This value changes with respect to the position and angle cuts made by the laser. The beam aperture will vary depending on the desired size of the protruding structure. In one example, the beam aperture can be 2.0 mm to create a protruding structure with a 1 $\mu$m diameter depression region. A 3.5 mm aperture will create a larger depression region. The intensity of the beam and dwell time can also be used to affect depression region size. Focus and nozzle height are set according to the size of the hypotube and the lamp intensity, which changes with use. In one embodiment, a focus of 9.38 and nozzle height of 0.368 inches (9.34 mm) is used. The beam expander is set to 7.0. The beam expander is used to change the angle the laser focuses onto the stent, which is used to adjust the focus of the laser beam at the stent surface. The beam expander allows the beam strength and beam diameter to be varied. As mentioned above, the beam diameter can also be varied by using the aperture. A low oxygen pressure, for example, 172 kPa, (26 PSI) is supplied when forming the holes. Of course, artisans will appreciate that the values given in the example (and throughout the description) are exemplary only, and not limiting.

To cut the stent pattern, the parameters of the laser system are typically altered. In one example, the stent is cut using a 1000 Hz pulse frequency and 0.075 millisecond pulse length. The power setting is 270 Volts to achieve 4.2 watts, and a 2.0 mm beam aperture in the beam path is used. The oxygen pressure has a high impact on cutting efficiency. For cutting the stent lattice pattern, high oxygen pressure, for example, 262 kPa (38 PSI), is used.

Often, cutting the lattice pattern into the stent, especially by laser, leaves scrap that must be removed, in a process known as descaling, to reveal the lattice pattern of the stent. Descaling is typically accomplished by ultrasonically cleaning the stent in heated acid, as described in U.S. Pat. No. 5,759,192.

After the holes are formed in the stent 100, the stent lattice pattern cut, and, if necessary, the stent descaled, a process of directing a pressurized stream of grit material upon the stent 100 is performed. Examples of such processes include bead blasting and sand blasting. Bead blasting refers to the use of pressurized gas to project beads of a relatively uniform diameter at an object at a high velocity. The beads may be made of a variety of materials, such as latex, aluminum oxide, or silicon oxide. In sand blasting, the grit projected does not have as uniform a diameter as in bead blasting. Both bead blasting and sand blasting are techniques that are well known in the art.

Figure 7:
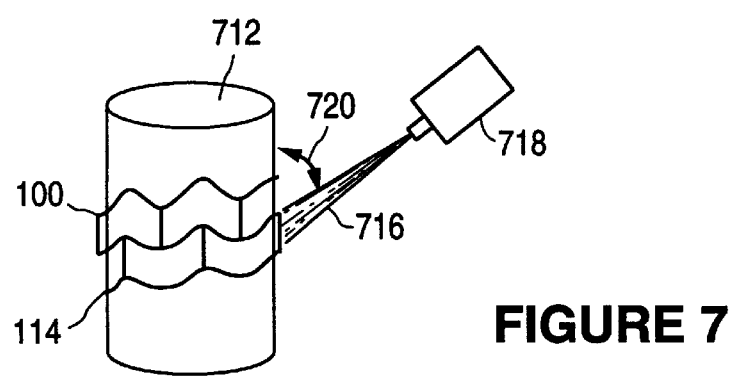
FIG. 7 is a schematic representation of the method of using a pressurized grit source in the process of forming protruding structures on the stent surface.

FIG. 7 illustrates use of the pressurized grit source to form one embodiment of the stent, in which the protruding structures are formed on the outer surface 114 of the stent 100. In FIG. 7, the stent 100 is mounted onto a mandrel 712. The stent is then rotated while the grit 716, e.g. beads, is projected at the stent outer surface from the pressurized grit source 718. The grit is projected at the stent at, for example, an approximately 30° angle 720 to the vertical axis of the stent, and is passed up and down over the outer surface 114 of the stent until the desired area of the stent, typically the area in which the holes have been formed, has been subjected to the stream. The visual appearance of the surface can be used to indicate that the blasted grit has been projected onto the area. The surface of the stent is smooth, shiny, and reflective before the bead or sand blasting process, but becomes dull, non-reflective, and of a darker color shade after the process. Subsequently, the stent is removed from the mandrel 712 and cleaned, for example by immersion and sonication in an isopropyl alcohol bath for approximately 20 minutes.

By way of example and not limitation, the grit can be beads having a diameter of between 1 $\mu$m and 50 $\mu$m. Pressures of, for example, 207 kPa (30 PSI) to, for example, 414 kPa (60 PSI) can be used to project the beads from a distance of, for example, approximately 3–10 cm from the stent. The grit source is passed very quickly, for example, in approximately 1–3 seconds, down and up over the stent in the areas of the stent that contain the holes.

In general, the shape of the protruding lip matches the shape of the hole formed with the laser. The shape of the protruding lip, for example the lip height, may be altered by changing, for instance, the hardness of the grit in relation to the hardness of the stent material, the speed the grit is projected, or the size and weight of the grit.

Figure 8A:
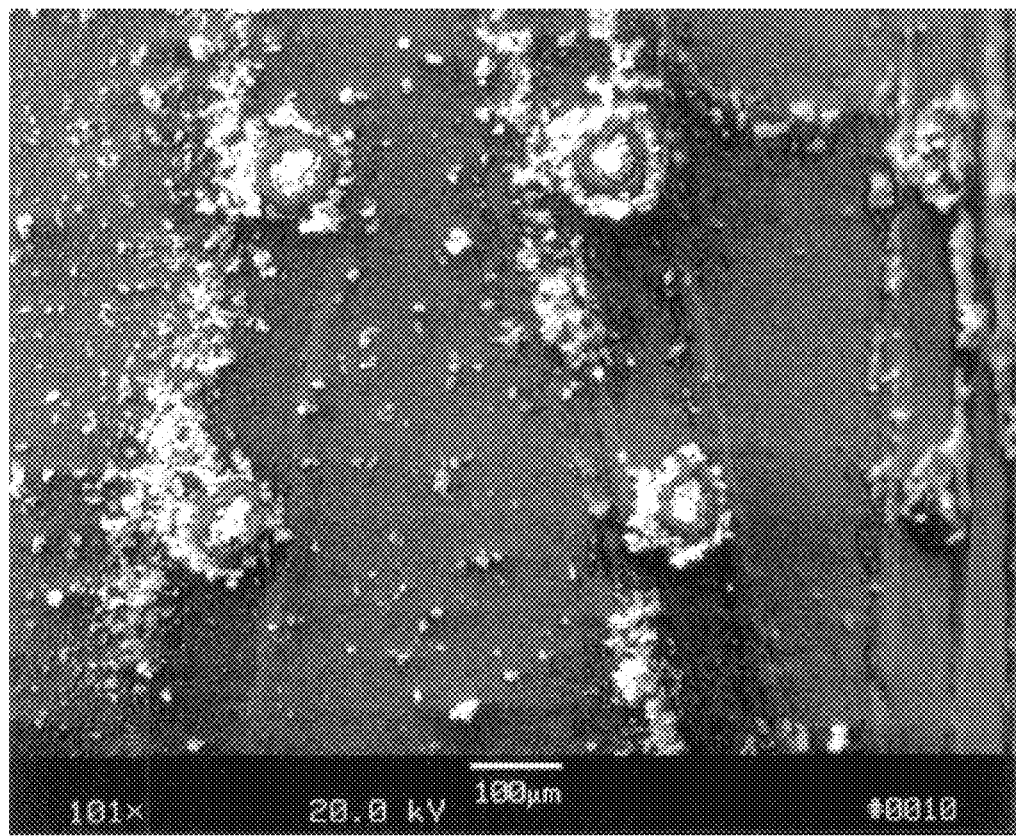
FIG. 8A is a scanning electron micrograph photograph of a portion of a stent with protruding structures on the stent struts.
Figure 8B:
FIG. 8B is a scanning electron micrograph photograph of a portion of a stent strut showing a protruding structure.

Scanning electron micrograph photographs of protruding structures that are craters and are formed by methods within the embodiments of the present invention are shown in FIGS. 8A and 8B. In these photographs, the stent has not yet been rinsed, for example in an alcohol bath as described above, and therefore beads from the bead blasting process (the white spheres) remain on the stent surface. In FIG. 8A, the stent is only partially descaled. Six protruding structures are shown, 2 on each of 3 stent struts in the photograph. FIG. 8B is a closer view of one of the protruding structures. The diameters 212, 214, and 216 of craters formed by this method typically are in the range of, for example, 20–100 $\mu$m. Depth 220 is typically in the range of, for example, 20–100 $\mu$m, and lip height 218 is typically in the range of, for example, 10–80 $\mu$m.

If desired, the stent surfaces that do not contain the protruding structures can be polished. For instance, it may be desirable to polish the inside surface 112 of the stent if the cover is to be attached to only the outside surface, as in, e.g., covered stent 530 of FIG. 5A, because the inside surface will be in contact with blood components. Polishing is typically accomplished by use of an abrasive slurry or electropolishing. However, these polishing methods may remove the protruding structures formed on the surface. Therefore, a temporary protective coating can be applied to the portions of the surface to be protected (the portions containing the protruding structures) during the polishing process. For example, a poly vinyl alcohol (PVA) solution (80% by weight dissolved in hot water at 100° C.) can be applied to the inner surface with a syringe and allowed to air dry. The temporary coating can be removed by soaking the coated stent in water. Polishing can be done either before or after the stream of pressurized grit is used. If polishing is done before the pressurized grit is applied, the holes in the stent must also be protected from the polishing process by use of a temporary coating.

As discussed above, the protruding structures can be of any shape in addition to the generally circular shapes shown in FIGS. 2A, 8A, and 8B. For instance, the protruding structures can have the exemplary shapes illustrated in FIGS. 3A, 3B, and 3C. The sizes of the protruding structures can also vary. One method of varying the size and shape of the protruding structure is to mask the laser pulse to produce holes in the stent having a desired shape and size. For example, masking can be used to form holes with small diameters, in the range of, for example, 1–10 $\mu$m. The small diameter holes will result in small diameter protruding structures once the blasting with pressurized grit has been performed. In another method, useful for forming, for example, ovular or groove shaped protruding structures, the stent can be rotated and the laser moved across the strut surface for the desired distance to form the hole of the desired shape. Pressurized grit is then directed at the stent surface as described above to form the protruding structures.

Therapeutic substance may be added to the depression region of the protruding structure using any suitable method. In an exemplary method the therapeutic substance is mixed with a solvent, for example, 0.011 g of actinomycin D is mixed with 1.5 g of tetrahydrofuran. The implantable medical device with the protruding structures is then dipped in the therapeutic substance and solvent solution allowing the solution to fill the depression regions of the protruding structures. The implantable medical device is removed from the solution and allowed to dry. Any excess therapeutic substance not in the depression region is removed by blowing air at, for example, 620 kPa (90 PSI) toward the implantable medical device at a 90° angle, with the end of the air nozzle at, for example, approximately 10 cm from the surface of the device.

A polymer layer can then be added by dipping the device into a polymer and solvent solution, or, if desired, a polymer, solvent, and therapeutic substance solution. The solution is allowed to dry and, if desired, air can be blown at the device (e.g. 620 kPa, nozzle 10 cm from device, 90° angle) to clean excess solution off of the device.

While particular embodiments of the present invention have been shown and described, it will be clear to those of ordinary skill in the art that changes and modifications can be made without departing from this invention in its broader aspects and, therefore, the appended claims are to encompass within their scope all such changes and modifications as fall within the true spirit and scope of this invention.

What is claimed is:

1. An implantable medical device comprising:
   a substrate having a first surface, said first surface having a plurality of protruding structures, wherein each of said protruding structures includes
      a depression region having a bottom surface, said depression region approximately centrally located in said protruding structure; and
      a lip surrounding at least a portion of said depression region, said lip having a height that extends above said bottom surface and said first surface.

2. The implantable medical device of claim 1, wherein said depression region and lip are substantially circular.

3. The implantable medical device claim 1, wherein said depression region and lip form a groove.

4. The implantable medical device of claim 1, wherein said substrate has a thickness defined by a distance between said first surface and an opposite second surface, said protruding structure has a depth defined by a distance between said bottom surface and said first surface, and said depth is less than 80% of said thickness.

5. The implantable medical device of claim 1, wherein said bottom surface is above said first surface.

6. The implantable medical device of claim 1, wherein said bottom surface is beneath said first surface.

7. The implantable medical device of claim 1 further comprising:
   a cover overlying said first surface, wherein said protruding structures engage said cover.

8. The implantable medical device of claim 7 further comprising glue located in said depression region of at least some of said protruding structures.

9. The implantable medical device of claim 7, wherein said cover comprises a therapeutic substance.

10. The stent of claim 1, wherein said depression region contains one or more therapeutic substances.

11. The stent of claim 10, wherein said one or more therapeutic substances is covered by a polymeric layer.

12. A stent comprising:
   a body having a generally cylindrical shape and an outer surface, wherein said outer surface includes a plurality of protruding structures, wherein said protruding structures include:
      a depression region having a bottom surface, said depression region approximately centrally located in said protruding structure; and
      a lip surrounding at least a portion of said depression region, said lip having a height that extends above said bottom surface and said outer surface.

13. The stent of claim 12 further comprising:
   a cover overlying said outer surface, wherein said protruding structures engage said cover.

14. The stent of claim 13, wherein said cover has a first end and an opposing second end, wherein said stent comprises a first section and a second section, and wherein said first section is attached to said first end of said cover and said second section is attached to said second end of said cover.

15. The stent of claim 13, further comprising glue located in said depression region of at least some of said protruding structures.

16. The stent of claim 13, wherein said cover comprises a therapeutic substance.

17. The stent of claim 12, wherein said depression region and said lip are substantially circular.

18. The stent of claim 17, wherein said depression region contains one or more therapeutic substances.

19. The stent of claim 18, wherein said one or more therapeutic substances is covered by a polymeric layer.

20. The stent of claim 12, wherein said depression region and said lip form a groove.

21. The stent of claim 20, wherein said groove contains one or more therapeutic substances.

22. The stent of claim 21, wherein said one or more therapeutic substances is covered by a polymeric layer.

23. The stent of claim 12, wherein said body has a thickness defined by a distance between said outer surface and an opposite inner surface, said protruding structure has a depth defined by a distance between said bottom surface and said outer surface, and said depth is less than 80% of said thickness.

24. The stent of claim 12, wherein said bottom surface is above said outer surface.

25. The stent of claim 24, wherein said depression region contains one or more therapeutic substances.

26. The stent of claim 25, wherein said one or more therapeutic substances is covered by a polymeric layer.

27. The stent of claim 12, wherein said bottom surface is beneath said outer surface.

28. The stent of claim 27, wherein said depression region contains one or more therapeutic substances.

29. The stent of claim 28, wherein said one or more therapeutic substances is covered by a polymeric layer.

30. The stent of claim 12, wherein said depression region contains one or more therapeutic substances.

31. The stent of claim 30, wherein said one or more therapeutic substances is covered by a polymeric layer.

* * * * *

UNITED STATES PATENT AND TRADEMARK OFFICE
CERTIFICATE OF CORRECTION

PATENT NO. : 6,254,632 B1
DATED : July 3, 2001
INVENTOR(S) : Steven Z. Wu et al.

Page 1 of 1

It is certified that error appears in the above-identified patent and that said Letters Patent is hereby corrected as shown below:

Column 13, claim 1,
Line 2, delete "An implantable medical device" and insert -- A stent --.

Column 13, claim 2,
Line 12, delete "implantable medical device" and insert -- stent --.

Column 13, claim 3,
Line 14, delete "implantable medical device" and insert -- stent --.

Column 13, claim 4,
Line 16, delete "implantable medical device" and insert -- stent --.

Column 13, claim 5,
Line 22, delete "implantable medical device" and insert -- stent --.

Column 13, claim 6,
Line 24, delete "implantable medical device" and insert -- stent --.

Column 13, claim 7,
Line 26, delete "implantable medical device" and insert -- stent --.

Column 13, claim 8,
Line 30, delete "implantable medical device" and insert -- stent --.

Column 13, claim 9,
Line 33, delete "implantable medical device" and insert -- stent --.

Signed and Sealed this

Twenty-sixth Day of March, 2002

*Attest:*

*Attesting Officer*

JAMES E. ROGAN
*Director of the United States Patent and Trademark Office*